United States Patent [19]

Schott et al.

[11] 4,258,186

[45] Mar. 24, 1981

[54] PROCESS FOR THE PREPARATION OF BLOCKED POLYISOCYANATES

[75] Inventors: Ansgar Schott, Bochum; Rainer Gras; Elmar Wolf, both of Herne, all of Fed. Rep. of Germany

[73] Assignee: Chemisch Werke Huls AG, Kreis Recklinghausen, Fed. Rep. of Germany

[21] Appl. No.: 961,562

[22] Filed: Nov. 17, 1978

[30] Foreign Application Priority Data

Nov. 19, 1977 [DE] Fed. Rep. of Germany ....... 2751805

[51] Int. Cl.$^3$ .......................................... C07D 403/12
[52] U.S. Cl. .................................. 544/253; 544/296; 544/242; 528/45
[58] Field of Search ........................ 544/296, 335, 253

[56] References Cited

U.S. PATENT DOCUMENTS

| | | | |
|---|---|---|---|
| 3,830,785 | 8/1974 | Matsui et al. | 528/45 |
| 3,846,442 | 11/1974 | Habermeier | 544/296 |
| 3,857,818 | 12/1974 | Frizelle | 525/124 |
| 4,096,291 | 6/1978 | Dunwald et al. | 427/120 |

*Primary Examiner*—Paul M. Coughlan, Jr.

*Attorney, Agent, or Firm*—Oblon, Fisher, Spivak, McClelland & Maier

[57] ABSTRACT

A process for the preparation of blocked polyisocyanates which comprises reacting a polyisocyanate with a cyclic amidine of the formula:

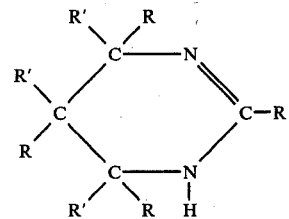

wherein R are the same or different substituents selected from the group consisting of hydrogen, alkyl, cycloalkyl, aralkyl and aryl, and wherein either R' and R or two R' taken together form a cycloaliphatic ring, and wherein the reaction is carried out at temperatures of 0°–150° C. Polyisocyanates blocked with 6-membered ring bicyclic amidines.

16 Claims, 10 Drawing Figures

PROCESS FOR THE PREPARATION OF BLOCKED POLYISOCYANATES

FIELD OF THE INVENTION

This invention concerns a process for the preparation of new compounds with a high latent isocyanate content as well as the compounds obtained by means of this process.

DESCRIPTION OF THE PRIOR ART

The preparation of masked isocyanates, also called isocyanate yielders, is known and described in Houben-Weyl: Methods of Organic Chemistry XIV/2, Page 61-70. Known blocking agents are tertiary alcohols, phenols, mercaptans, acetoacetic esters, malonic acid esters, acetic acetone, imides, such as phthalimide, imidazoles, hydrochloric acid, hydrocyanic acid and ε-caprolactam. In practice, the use of monophenols and ε-caprolactam is preferred for this purpose.

These masked isocyanates have the property of reacting like isocyanates at a higher temperature. The splitting of the blocking agent is easier, the more acidic the H-atom of the masking group. Blocked isocyanates of this type are described in DT-OS 21 66 423. Blocked end-isocyanates, which in addition contain uretdion-groups, are also described in DT-OS 25 02 934.

The most significant disadvantage in regard to the use of these blocking agents is the relatively high splitting temperature in a number of applications, which for most phenols, in the case of aliphatic polyisocyanates, is at least 190° C.; in the case of aromatic polyisocyanates, about 30° C. lower. The splitting temperature of aliphatic ε-caprolactam-blocked polyisocyanates is, for example, generally at about 180°-190° C.

For this reason, it was suggested in the past to use thiophenols, for which this temperature is much lower. However, the disadvantage of the thiophenols is their extremely unpleasant odor.

It was also suggested to add 1-2 percent of a catalyst by means of which the splitting temperature could be reduced to 125°-140° C. However, this has an unfavorable effect on the usability span of the unhardened coating material.

SUMMARY OF THE INVENTION

Surprisingly, it was now found that it is possible to, in a simple manner, prepare blocked polyisocyanates which unblock at a temperature that is at least 20°-30° C. lower than the isocyanates masked by the conventional blocking agents, if the process for the preparation of blocked polyisocyanates by the reaction of polyisocyanates with N-containing cyclic compounds is carried out in such a way that, as the N-containing cyclic compound, one uses cyclic amidines of the general formula in which R may be like or unlike substituents of the hydrogen-, alkyl-, cycloalkyl-, aralkyl- and aryl-group, and R', R or 2 R' together may be a constituent of a cycloaliphatic ring, and the reaction takes place at temperatures of 0°-150° C., preferably of 80° to 120° C.

BRIEF DESCRIPTION OF THE DRAWINGS

A more complete appreciation of the invention and many of the attendant advantages thereof will be readily obtained as the same becomes better understood by reference to the following detailed description, when considered in connection with the accompanying drawings, wherein:

FIG. 1 is the infrared spectrum of the blocked polyisocyanate obtained in Example 2a;

FIG. 4 is the infrared spectrum of the blocked polyisocyanate adduct obtained in Example 4a;

FIG. 5 is the infrared spectrum of the blocked polyisocyanate obtained in Example 6a;

FIG. 8 is the infrared spectrum of the blocked polyisocyanate obtained in Example 7a;

FIG. 9 is the infrared spectrum of the blocked polyisocyanate obtained in Example 9a;

DETAILED DESCRIPTION OF THE PREFERRED EMBODIMENTS

The polyisocyanates and the cyclic amidines are used in such quantities that there are 0.5-1.1, preferably 0.8-1.0, moles, of cyclic amidine per one isocyanate group.

Suitable as starting compounds that can be used for blocking with the cyclic amidines are, for example, polyisocyanates, especially diisocyanates, such as aliphatic, cycloaliphtic, araliphatic, i.e. aryl-substituted aliphatic and/or aromatic diisocyanates as they are, for example, described in Houben-Weyl, Methods of Organic Chemistry, Volume 14/2, Page 61-70, and in the article by W. Siefken in Justus Liebig's Annals of Chemistry 562, 75 to 136, such as 1,2-ethylene diisocyanate, 1,4- tetramethylene diisocyanate, 1,6-hexamethylene diisocyanate, 2,2,4-or 2,4,4-trimethyl-1,6-hexamethylene diisocyanate (TMDI), 1,12-dodecandiisocyanate, ω, ω'-diisocyanatodipropylether, cyclobutane-1,3-diisocyanate, cyclohexane-1,3- and 1,4-diisocyanate, 2,2- and 2,6-diisocyanato-1-methylcyclohexane, 3-isocyanatomethyl-3,5,5-trimethylcyclohexylisocyanate, which is also called isophorondiisocyanate and abbreviated IPDI, decahydro-8-methyl-(1,4-methano-naphthalene-2 (or 3)) -5-ylendimethylene-diisocyanate, hexahydro-4,7-methano-indan-1 (or 2) -5- (or 6) - ylendimethylene-diisocyanate, hexahydro-4,7-methaneindan-1-(or 2) -5- (or 6)-ylen-diisocyanate, dicyclohexyl-4,4'-diisocyanate, dicyclohexyl-2,4'-diisocyanate, 2,4- and 2,6-hexahydrotoluylene-diisocyanate, perhydro-2,4'- and/or -4,4'-diphenylmethane-diisocyanate, ω,ω,'-diisocyanato-1,4-diethylbenzene, 1,3- and 1,4-phenylendiisocyanate, 4,4'-diisocyanatodiphenyl, 4,4'-diisocyanato-3,3'-dichlordiphenyl, 4,4'-diisocyanato-3,3'-dimethoxy-diphenyl-4,4'- diisocyanato-3,3'-dimethyl-diphenyl, 4,4'-diisocyanato-3,3'-diphenyl- diphenyl, 2,4'- and 4,4'-diisocyanato-diphenyl-methane, naphthylene-1,5- diisocyanate, toluylene diisocyanate, 2,4 or 2,6-toluylene-diisocyanate, N,N'- (4,4'-dimethyl-3,3'-diisocyanatodiphenyl)-uretdion, m-xylylene-diisocyanate, but also the triisocyanates, such as 2,4,4'-triisocyanato-diphenyl-ether, 4,4',4''-triisocyanatotriphenylmethane, tris-(4-isocyanatophenyl)-thiophosphate, as well as appropriate mixtures of these isomers. Other suitable isocyanates are described in the mentioned article in the Annals on Page 122.

As a rule, the technically easily accessible aliphatic, cycloaliphatic or aromatic diisocyanates are preferred, and especially the 3-isocyanatomethyl-3,5,5-trimethyl-cyclohexylisocyanate and 2,4 or 2,6-toluylenediisocyanate and their isomeric mixtures.

The dimeric and trimeric forms of the polyisocyanates, such as uretdions and isocyanurates, which can be prepared according to the known methods, may naturally also be used as starting materials for the blocking with the tetrahydropyrimidines, which are described in detail in the following, in addition to the monomeric polyisocyanates.

Polyisocyanates within the meaning of this invention are also those which, before the blocking with the tetrahydropyrimidines, were subjected to a reaction, for the purpose of molecular enlargement, with the so-called chain extension agents customary in isocyanate chemistry, such as water, polyols, polyamines and others, in which case the bi- or trifunctional chain extension agent, which are those with 2 or 3 groups that can react with isocyanate groups such as compounds carrying hydroxyl- and/or amino-groups, is used in such quantities that the resulting new isocyanate on the average carries at least 2 isocyanate groups. When water is used as the chain extension agent, polyisocyanates with one or several urea groupings are obtained. The molecular weights of the suitable chain extension agents are expediently between 18 and 250.

Suitable polyols are, for example, diols and triols, such as ethylene glycol, propylene glycols, like 1,2- and 1,3 propane diol, 2,2-dimethylpropane diol- (1,3), butanediols, like butanediol-(1,4), hexanediols, like hexanediol-(1,6), 2,2,4-trimethylhexanediol- (1,6), 2,4,4-trimethylhexanediol-(1,6), heptanediol-(1,7), octadecene-9,10-diol-(1,12), thiodiglycol, octadecanediol-(1,18), 2,4-dimethyl-2-propylheptanediol-(1,3), butene- or butynediol-(1,4), diethylene glycol, triethylene glycol, tetraethylene glycol, trans- and cis-1,4-cyclohexanedimethanol, 1,4-cyclohexanediols, glycerin, hexane triol-(1,2,6), 1,1,1-trimethylolpropane, 1,1,1-trimethylolethane and others. Mixtures of the above-mentioned compounds may also be used.

Of the polyamines which are suited for the chain extension or molecular enlargement, the ethylenediamine-1,2, propylene diamine-1,2 and -1,3, butylene diamine-1,2, -1,3 and -1,4 as well as the hexamethylene diamines are useful, which polyamines may also carry one or several $C_1$-$C_4$ alkyl residues.

The reaction of the polyisocyanates before the blocking with the mentioned chain extension agents in the indicated proportions may be carried out at temperatures in the range of from 0°-150° C., preferably from 80°-120° C.

Suitable tetrahydropyrimidine derivatives within the meaning of the present invention, which correspond to the previously described general formula, are, for example, those which, if necessary, have aryl-substituted alkylresidues, and, if necessary, alkyl-substituted aryl-residues, such as 2-methyltetrahydropyrimidine, 2,4- (5 or 6), dimethyltetrahydropyrimidine, 2-ethyltetrahydropyrimidine, 2-ethyl-4-methyl-tetrahydropyrimidine, 2-benzyl-tetrahydropyrimidine, 2-phenyl-tetrahydropyrimidine, 2-phenyl-4 (5 or 6) -methyl-tetrahydropyrimidine, 2,4-diaza-3-phenyl-7,9,9- (or 7,7,9)-trimethyl-bicyclo-(4.3.0)-nonene-(2), 2,4-diaza-3-methyl-7,9,9- (or 7,7,9)-trimethyl-bicyclo-(4,3,0)-nonene-(2) and others.

Mixtures of the tetrahydropyrimidine derivatives may also be used according to the invention. This is particularly practical when blocked isocyanates with low melting points or ranges are required.

The tetrahydropyrimidine-derivatives that can be used according to the invention may be prepared, according to known processes, if necessary from substituted 1,3-diamines and aliphatic or aromatic monocarboxylic acids, mononitriles or monocarboxylic acid esters, if necessary, in the presence of elementary sulfur or sulfuryl chloride as the catalyst. The reason for the fact that these cyclic amidines have, until now, not been specified as blocking agents for NCO-groups, is perhaps that one could not expect right from the start that cyclic amidines would react with the NCO-groups to urea groups in such a smooth manner, since it is known that the —C≡N grouping in the tetrahydropyrimidines reacts with the NCO-groups while forming a triazine ring according to the following scheme.

in which R" is a bivalent organic residue, such as an alkylene, cycloalkylene or arylene residue.

As already mentioned, the blocking may also be carried out in solvents. The solvents for this reaction may only be those which do not react with the polyisocyanates, for example, ketones, such as acetone, methylethylketone, methylisobutylketone, cyclopentanone, cyclohexanone, and others; aromatic substances, such as benzene, toluene, xylenes, chlorobenzene, nitrobenzene, and others; cyclic ethers, such as tetrahydrofuran, dioxane, and others; esters, such as methylacetate, n-butylacetate, and others; aliphatic chlorinated hydrocarbons, such as chloroform, carbon tetrachloride, and others; as well as aprotic solvents, such as dimethylformamide, dimethylacetamide, dimethylsulfoxide, etc.

When the blocking agent is used at a ratio ≧1 to the number of isocyanate groups, the reaction mixtures are maintained at the indicated temperatures until the NCO-content of the reaction mixture has fallen to values below 0.2% NCO; for the ratio <1 until a constant NCO-value is reached.

Another result of this invention is the subsequent reaction of a group of blocked polyisocyanates, namely those in which the cyclic amidines were used in substoichiometric quantities, i.e., the ratio cyclic amidine:isocyanate groups was <1:1, with the same chain extension agents, which were described earlier as means for the molecular enlargement. The reaction also takes place at temperatures in the range of 0°–150° C., preferably 80°–120° C., but below the unblocking temperature of the blocked polyisocyanate. By means of this variant of the process, the range of products of the blocked polyisocyanates can be adapted to the practical requirements to a very large degree. This variant of the process is of special interest for polyisocyanates with NCO-groups of different reactivity, i.e., asymmetric polyisocyanates.

Thus, by changing the sequence adduct formation/-blocking, blocked isocyanates of varying reactivity, melting range and structure are obtained.

Another result of the invention are the adducts obtained according to the described processes, the general formulas of which are specified in the claims. These are generally compounds of the molecular weight range of 250–3000, preferably 300–1000. These products have a melting range at temperatures from 30°–220° C., preferably 80°–160° C. It is another characteristic of the invention that the polyisocyanates blocked by the cyclic amidines have a content of end-isocyanate-groups which are present in blocked form (calculated as NCO), of 4–26 weight %, preferably 7–23 weight %.

The compounds of the above-described invention, because of their melting points with at the same time higher molecular weights, are especially suitable as catalysts for the anionic polymerization of ε-caprolactam. The compounds may also be used for the production of wire lacquers.

Having generally described this invention, a further understanding can be obtained by reference to certain specific examples which are provided herein for purposes of illustration only and are not intended to be limiting unless otherwise specified.

EXAMPLE 1

1. Preparation of the Tetrahydropyrimidine—Isomer Mixture 312 g of an isomer mixture of 1-amino-2-aminomethyl-3,3,5 or 3,5,5-trimethylcyclopentane (TMCPD) were mixed with 136 g benzoic acid methyl ester and while being stirred, were heated in a reactor to 190° C. The reaction time was 2 hours. Subsequently, the diamine excess, together with the splitting products methanol and water, was distilled off. In the vacuum, at 0.1 Torr*, an isomer mixture of bicyclic tetrahydropyrimidines in a yield of 208 g ≙ 86% could be distilled at a temperature range of 158°–170° C.

*Torr=1 mm Hg pressure

The viscous yellow product is a mixture of compounds of the following formulas

The C/H/N-analysis resulted in the following values: 79.13% C, 9.3% H, 11.75% N,
(theory: 79.34% C, 9.09% H, 11.57% N).
NH$_2$-content: 4.11 mMol NH$_2$/g (theor. 4.13).
MG: 243.3 (theor. 242).

2. Isocyanate Blockings 2a. 484 g of the bicyclic isomer mixture according to example 1, in a flask, were heated to 100° C. Within a period of 90 minutes, 222 g of 3,3,5 or 3,5,5-trimethyl-1-isocyanato-3-isocyanatomethylcyclohexane (IPDI) (1:1) were added drop by drop. During this time, the viscosity increased significantly. In order to complete the reaction, the mixture was heated for another 180 minutes to 130° C.

Figure 1:
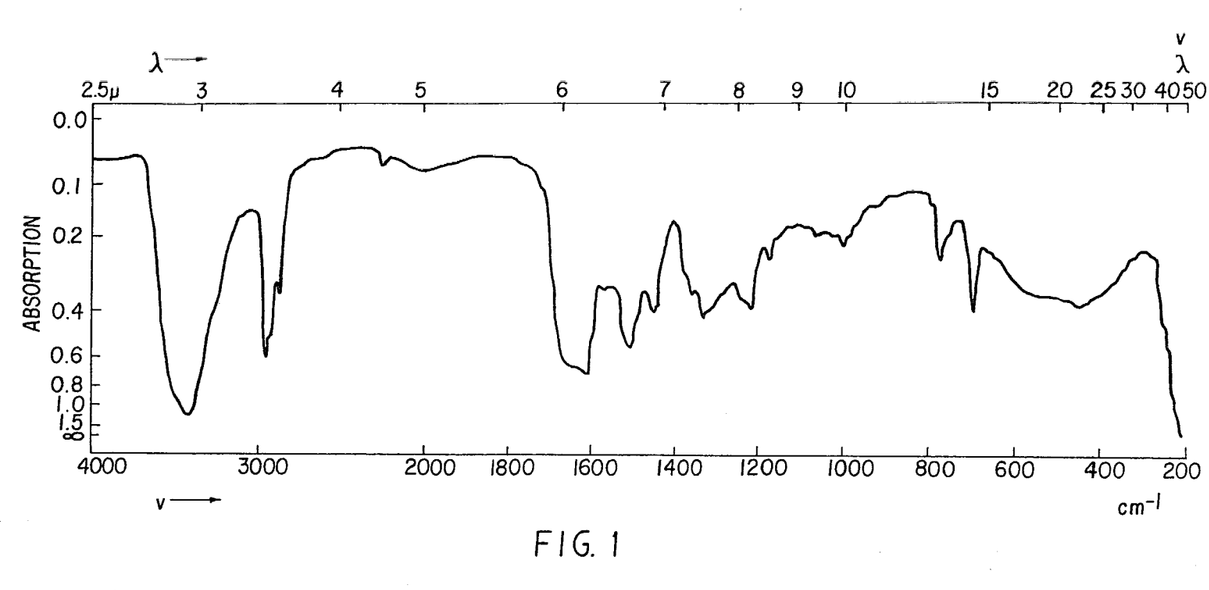

The glass transition point (DTA) of the resulting mixture was at 67°–75° C., the melting range at 85°–98° C. and the splitting temperature at about 160° C. The IR-spectrum of the blocked polyisocyanate is shown in Illustration 1.

Figure 2:
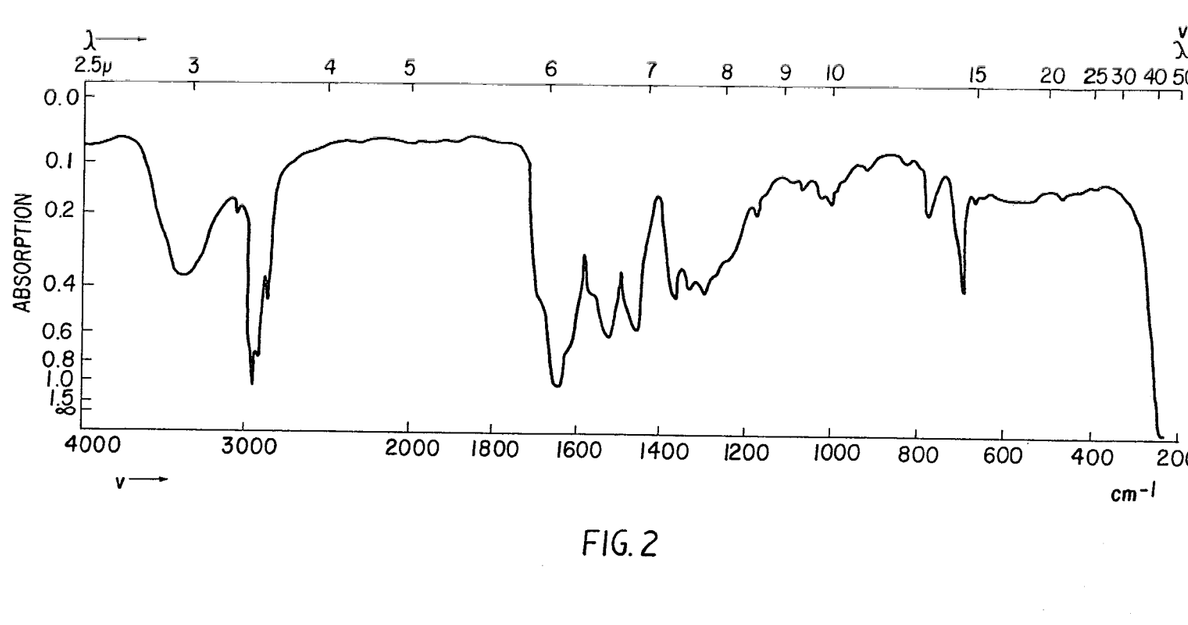
FIG. 2 is the infrared spectrum of the blocked polyisocyanate obtained in Example 2b.

2b. Analogous to Example 2a, the corresponding isocyanate adduct was prepared from 210 g 2,2,4- or 2,4,4- trimethylhexamethylenediisocyanate (TMDI) (1:1), 484 g of the mixture from Example 1, at 100° C. Melting range: 75°–89° C., softening point (DTA): 52°–75° C., splitting temperature: 160° C. The IR-spectrum of the blocked polyisocyanate is shown in Illustration 2.

Figure 3:
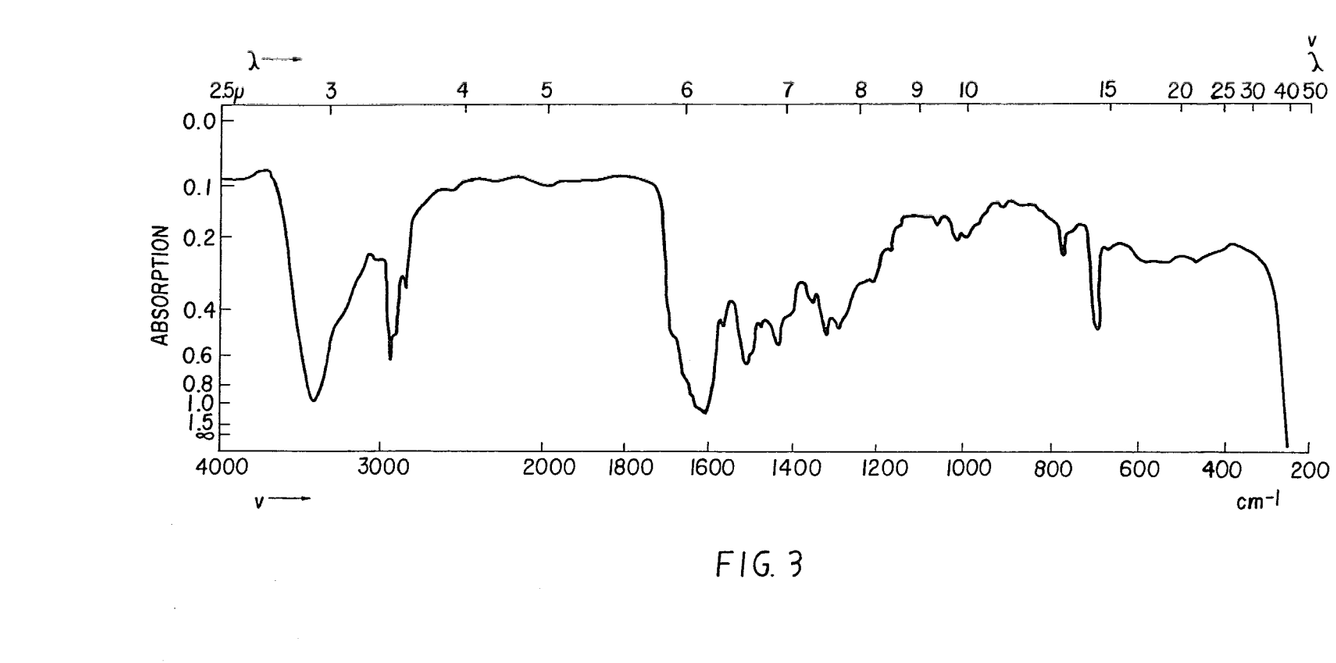
FIG. 3 is the infrared spectrum of the blocked polyisocyanate obtained in Example 2c.

2c. Analogous to Example 2a, the corresponding isocyanate adduct was prepared from 175 g toluylene-2,4-(2,6)-diisocyanate (TDI) (from 80% 2,4 and 20% 2,6) and 484 g of the mixture from Example 1, at 120° C.; yellow powder. Melting range 93–105%, softening point (DTA) 71°–89° C., splitting temperature 150° C. The IR spectrum of the obtained blocked polyisocyanate is shown in Illustration 3.

EXAMPLE 3: Preparation of the Diethylene Glycol/Isocyanate Adducts

3a. To 444 g IPDI, according to Example 2a, were slowly added 106 g diethylene glycol at 80° C., stirring thoroughly. After the adding of the diethylene glycol, heating was continued for 2 h at 80° C. The NCO-content of the adduct was then 15.1%.

3b. To 420 g TMDI, according to Example 2b, were slowly added 106 g diethylene glycol at 90° C., stirring thoroughly. After the adding of the diethylene glycol, heating was continued for 2 h at 90° C. The NCO-content of the adduct was then 16.0%.

3c. To 348 g TDI, according to Example 2c, were slowly added 106 g diethylene glycol at 95° C., stirring thoroughly. After the adding of the diethylene glycol, heating was continued for 2 h at 90° C. The NCO content of the adduct was then 18.5%.

EXAMPLE 4: Blocked Isocyanate Adducts

4a. To 550 g of the adduct described in Example 3a of 2 moles IPDI and 1 mole diethylene glycol were added 484 g of the mixture according to Example 1, at 120° C. in such a way that the temperature did not rise above 125° C. After the adding, the reaction mixture was heated for another 2 h at 120° C.

Figure 4:
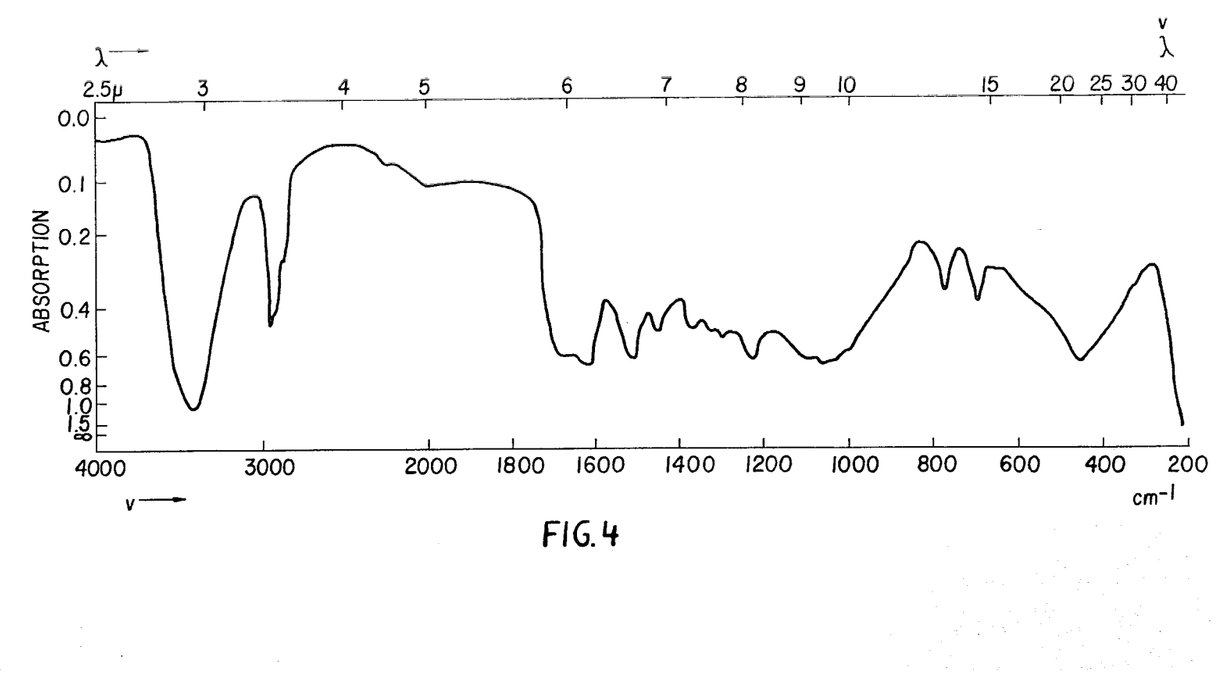

No more NCO could be identified in the reaction product obtained in this manner. The reaction product is a yellowish powder with a melting range of 89°–101° C. and a softening point (DTA) of 75°–86° C. with a splitting temperature of 170° C. The IR spectrum of the obtained blocked polyisocyanate adduct is shown in Illustration 4.

4b. Analogous to Example 4a, 526 g of the adduct described in Example 3b of 2 moles TMDI and 0.1 mole diethylene glycol were reacted with 484 g of the mixture according to Example 1 at 120° C. The reaction product is brittle and has a yellow color. Melting range 77°–93° C., softening point (DTA) 69°–79° C., splitting temperature 170° C.

4c. Analogous to Example 4a, 454 g of the adduct described in example 3c were reacted with 484 g of the mixture according to example 1, at 135° C. Melting range 93°–107° C., softening point (DTA) 79°–92° C., splitting temperature 160° C.

EXAMPLE 5: Preparation of Another Tetrahydropyrimidine Mixture 216 g ethyl acetate and 1248 g TMCPD - isomer mixture (mole ratio 1:4) were filled into a pressure reactor while being stirred and were reacted for 2.5 hours at 190° C. and 6.5 bar. After removal of the excess TMCPD and of the splitting products by distillation, an isomer mixture with tetrahydropyrimidine structure could be isolated in the vacuum (0.5 Torr (Torr=1 mm Hg pressure)) at 100°–119° C. Yield: 274 g ≙ 76% of the part.

The highly viscous product has a yellow color and contains compounds of the following formulas Equivalent weight: 183, theory: 180.
Determined: 73.12% C, 10.89% H, 15.45% N.
Theory: 73.33% C, 11.11% H, 15.55% N.

EXAMPLE 6: Isocyanate Blocking

Figure 5:
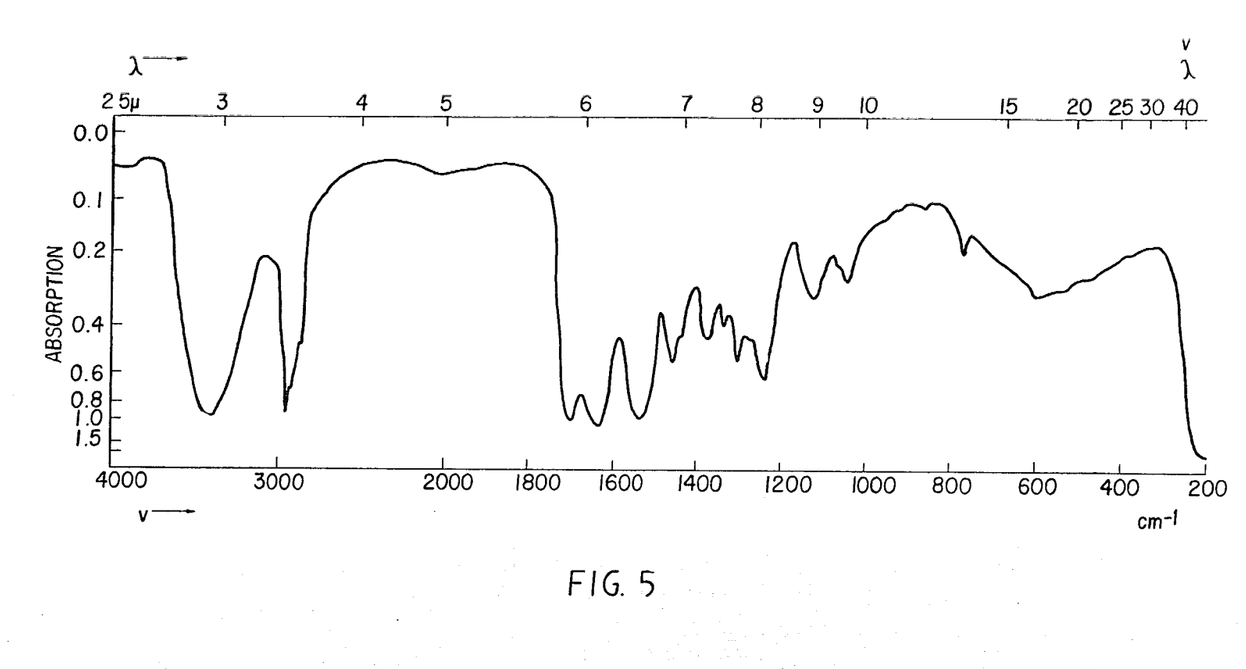

6a. To 360 g of the mixture according to Example 5 were added 222 g IPDI according to Example 2a, drop by drop, in such a way that the temperature in the reaction flask did not rise above 120° C. In order to complete the reaction, the reaction mixture was maintained at 120° C. for another 3 hours. These conditions were sufficient for an almost complete reaction. The reaction product is a yellowish, crystalline powder with a melting range of 95° to 104° C., a softening point (DTA) of 59°–74° C. and a free NCO-content of 0.1%. The splitting temperature was at 180° C. The IR spectrum of the blocked polyisocyanate is shown in Illustration 5.

Figure 6:
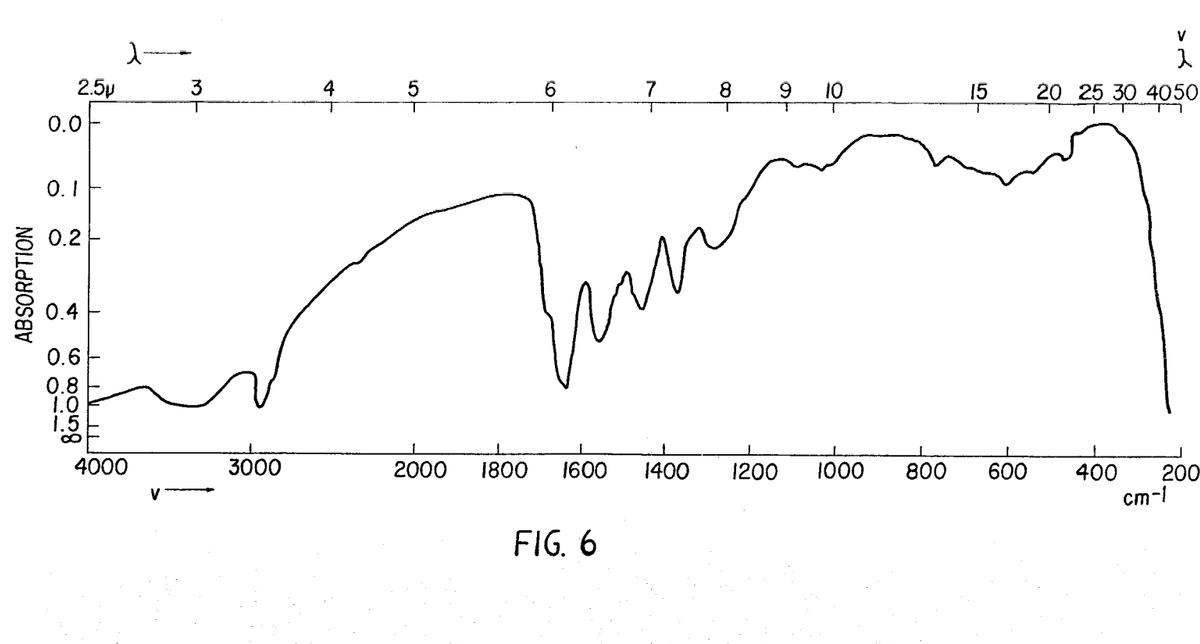
FIG. 6 is the infrared spectrum of the blocked polyisocyanate obtained in Example 6b.

6b. To 360 g of the mixture according to Example 5 were added 210 g TMDI according to Example 2b, drop by drop, in such a way that the temperature in the reaction flask did not rise above 120° C. In order to complete the reaction, the reaction mixture was maintained at 120° C. for another 3 hours. The conditions were sufficient for a complete reaction. The reaction product had a melting range of 84°–95° C., a softening point (DTA) of 50°–69° C. and a free NCO-content of 0.1%. The splitting temperature was at about 170° C. The IR spectrum of the blocked polyisocyanate is shown in Illustration 6.

Figure 7:
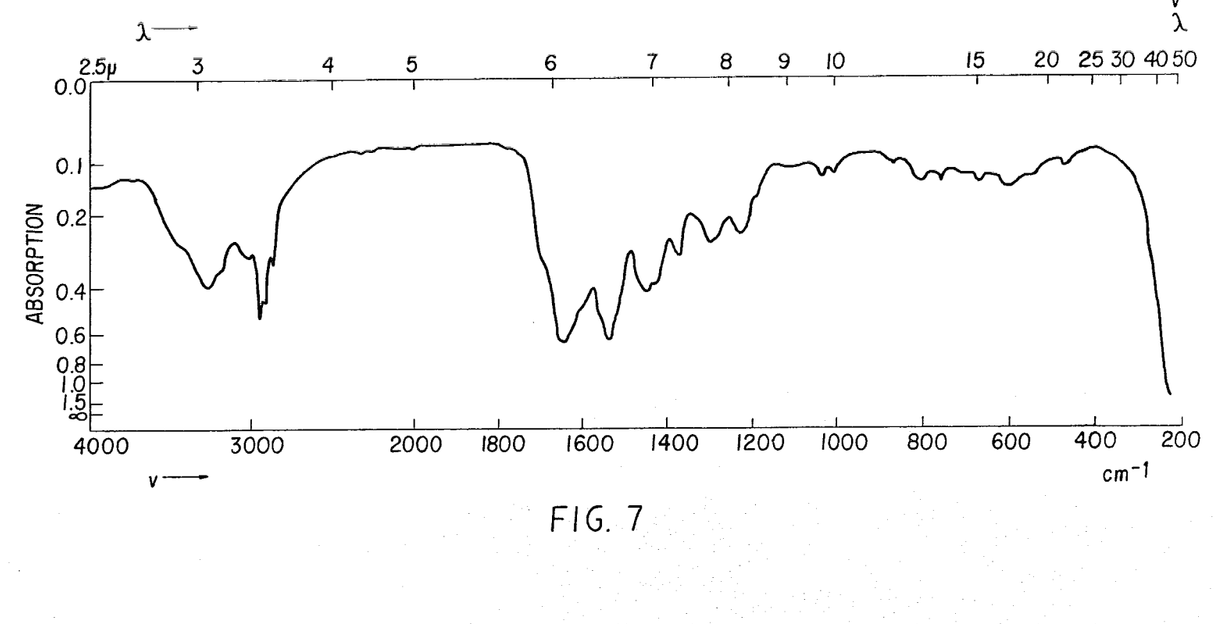
FIG. 7 is the infrared spectrum of the blocked polyisocyanate obtained in Example 6c.

6c. Analogous to Example 6a, the corresponding isocyanate product was prepared from 360 g of the mixture according to Example 5 and 174 g corresponding to Example 2c at 125° C.: Yellow reaction product, melting range: 98°–111° C., softening point (DTA) 70°–91° C., splitting temperature 170° C. The IR spectrum of the blocked polyisocyanate is shown in Illustration 7.

EXAMPLE 7: BLocked Isocyanate Adducts

Figure 8:
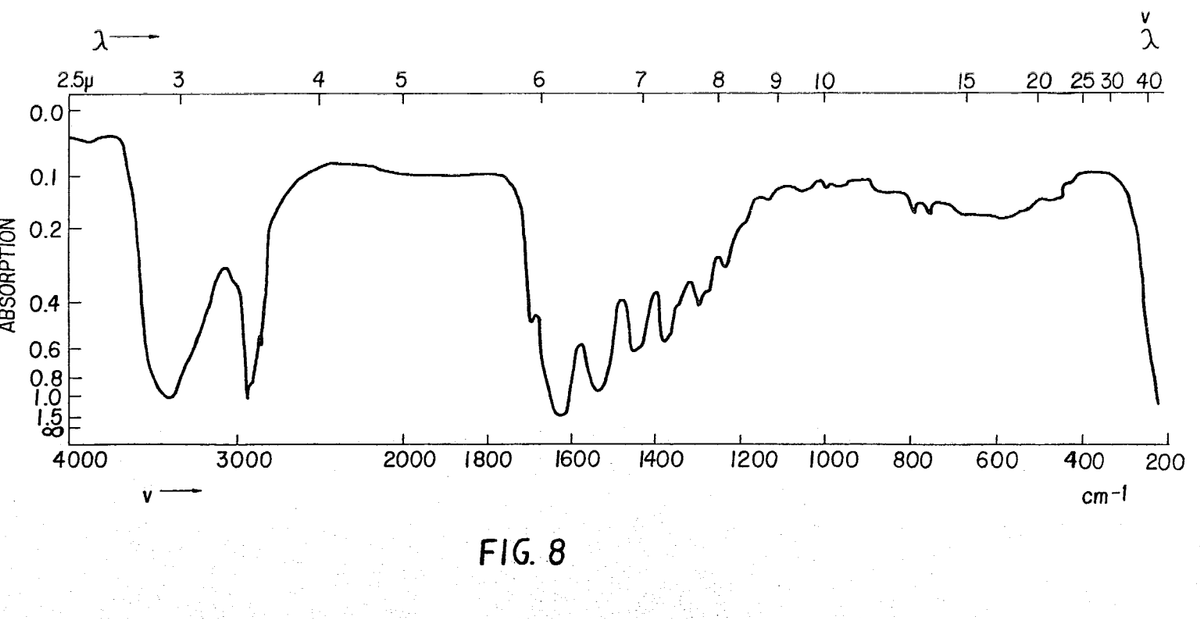

7a. To 550 g of the adduct described in Example 3a of 2 moles IPDI and 1 mole diethylene glycol were added, drop by drop, 360 g of the mixture according to Example 5 in such a way that the temperature did not exceed 130° C. After the adding, the reaction mixture was maintained for another 2 hours at 130° C. No more NCO could be identified in the reaction product prepared in this manner. The reaction product is a colorless powder with a melting range of 103°–113° C., a softening point of 77°–92° C. and a splitting temperature of 190° C. The IR-spectrum of the blocked polyisocyanate is shown in Illustration 8.

7b. To 526 g of the adduct described in Example 3b were added 360 g of the mixture according to Example 5 in such a way that the temperature did not rise above 130° C. After the adding, the reaction mixture was maintained for another 2 hours at 130° C. The reaction product is a yellowish, NCO-free powder with a melting range of 98°–106° C., a softening point (DTA) of 69°–88° C. The splitting temperature was at 180° C.

7c. Analogous to Example 7a, 454 g of the adduct described in Example 3c of 2 moles TDI and 1 mole diethylene glycol were reacted with 360 g of the mixture according to Example 5 at 140° C. The reaction product has a yellow color. Melting range 112°–120° C., softening point (DTA) 89°–101° C., splitting temperature: 170° C.

EXAMPLE 8: Preparation of 2-Phenyl-Tetrahydropyrimidine

With 185 g 1,3-diaminopropane, 136 g benzoic acid methyl ester were reacted under pressure at 200° C. in the reactor. After 3 hours, the excess of diamine was distilled off, and the 2-phenyl-tetrahydropyrimidine was isolated in a 79% yield. Boiling point 165° C./1 mm; melting point=86°–87° C.

EXAMPLE 9: Isocyanate Blocking

Figure 9:
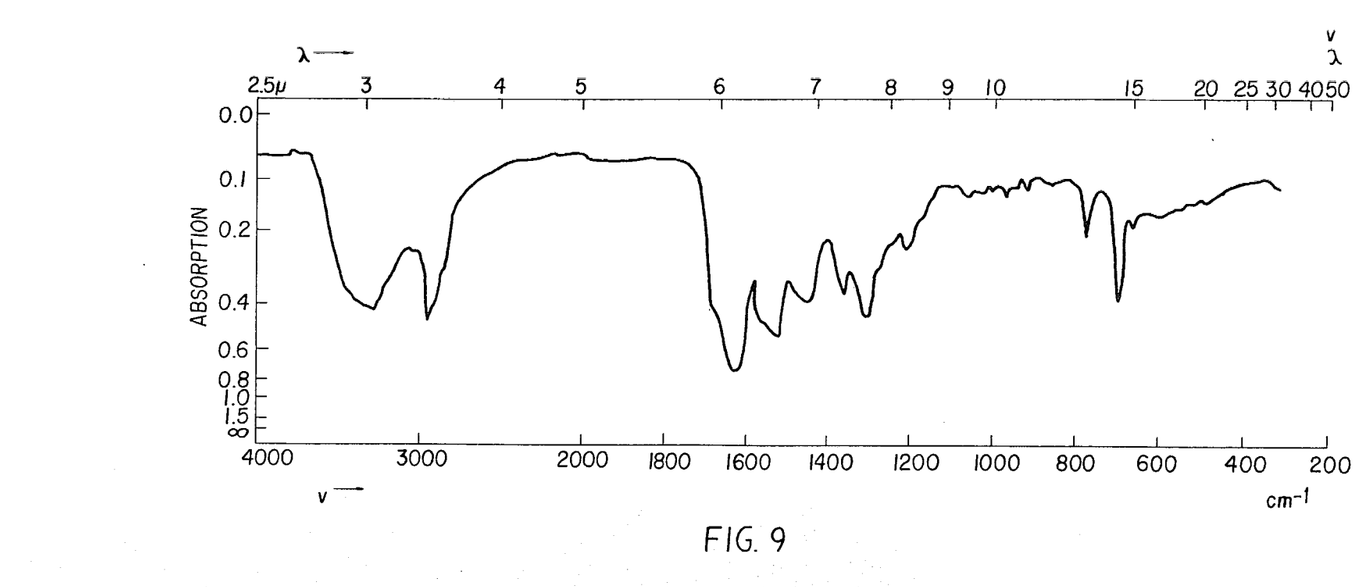

9a. To 338 g 2-phenyltetrahydropyrimidine were added, drop by drop, 222 g IPDI according to Example 2a in such a way that the temperature in the reaction flask did not exceed 120° C. The mixture was maintained at 120° C. for another 3 hours. The melting point of the yellow powder was at 71°–85° C., softening point (DTA) 48°–65° C., splitting temperature 160° C., NCO-content 0.1%. The IR-spectrum of the blocked polyisocyanate is shown in Illustration 9.

Figure 10:
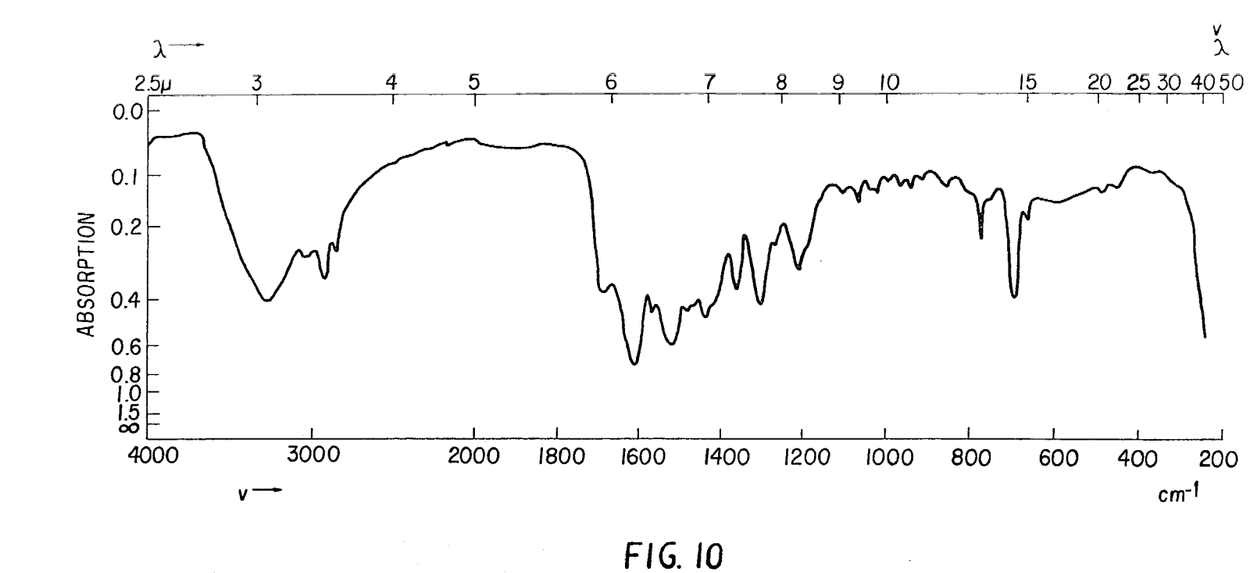
FIG. 10 is the infrared spectrum of the blocked polyisocyanate obtained in Example 9b.

9b. A 50% acetonic solution of 174 parts by weight tolyulene diisocyanate (TDI) according to Example 2c was added, drop by drop, to a 50% acetonic solution of 338 g 2-phenyl-tetrahydropyrimidine at boiling heat and heated for 2 hours under reflux. After the acetone was distilled off, a light-yellow powder was obtained. Melting range: 68° to 91° C., softening point (DTA) 52°-68° C., splitting temperature: 160° C., NCO-content <0.2%. The IR-spectrum of the blocked polyisocyanate is shown in Illustration 10.

EXAMPLE 10: Preparation of the 2-Phenyl-4 or 6-methyltetrahydropyrimidine—Isomer Mixture 52.8 g 1,3-diaminobutane were reacted with 27.2 g benzoic acid methyl ester under pressure at 200° C. in the reactor. After 3 hours, the diamine excess was distilled off, and the 2-phenyl-4- or 6-methyltetrahydropyrimidine was isolated in a 68% yield. Boiling point 0.05, equivalent weight 182 (theory 174).

EXAMPLE 11: Isocyanate Blocking

To 36.6 g of the isomer mixture according to Example 10 were added 22.2 g IPDI according to Example 2a at 120° C., drop by drop, and were maintained at this temperature for 3 hours. The melting range of the yellow product was at 70°-83° C., softening point (DTA) 43° to 58° C., splitting temperature 180° C., NCO-content <0.2%.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. In a process for the preparation of blocked polyisocyanates which comprises reacting a polyisocyanate with a blocking agent, the improvement wherein said blocking agent is a cyclic amidine of the formula:

wherein R and R' are the same or different substituents selected from the group consisting of hydrogen-, alkyl-, cycloalkyl-, benzyl and phenyl and wherein either R' and R, or 2 R' taken together form a cycloaliphatic ring, and wherein the reaction is carried out at temperatures of 0°-150° C.

2. A process according to claim 1, wherein the polyisocyanates and the cyclic amidines are used in such quantities that for one isocyanate group there is 0.5-1.1, mole cyclic amidine.

3. A process according to claim 2, wherein when the blocked polyisocyanates have been prepared using cyclic amidines in substoichiometric quantities, said blocked polyisocyanates are subsequently subjected to reaction with polyvalent chain extension agents having 2 or 3 groups which are reactive with isocyanate groups, at temperatures in the range 0°-150° C., but below the unblocking temperature.

4. A process according to claim 3, wherein the reaction is carried out at temperatures in the range of 80°-120° C.

5. A process according to claim 3, wherein the chain extension agent is water.

6. A process according to claim 3, wherein the chain extension agents are polyols.

7. A process according to claim 3, wherein the chain extension agents are polyamines.

8. A blocked polyisocyanate of the formula wherein R and R' are the same or different substituents selected from the group consisting of hydrogen-, alkyl-, cycloalkyl-, benzyl and phenyl and wherein either R' and R or 2 R' taken together form a cycloaliphatic ring.

9. A blocked polyisocyanate of the formula:

wherein R and R' are the same or different substituents selected from the group consisting of hydrogen, alkyl, cycloalkyl, benzyl and phenyl and wherein either R' and R or 2 R' taken together form a cycloaliphatic ring, and R" is an alkylene or cycloalkylene organic residue of a compound with 2 OH-groups which are reactive with isocyanate groups.

10. Blocked polyisocyanates of the formula wherein R and R' are the same or different substituents selected from the group consisting of hydrogen-, alkyl-, cycloalkyl-, benzyl and phenyl wherein R' and R or 2 R' taken together form a cycloaliphatic ring.

11. Blocked polyisocyanates of the formula wherein R''' is hydrogen, alkyl or a phenyl group.

12. The process of claim 1 wherein said blocking reaction is carried out at a temperature of 80°-120° C.

13. A process according to claim 2 wherein said polyisocyanate and said cyclic amidine are reacted in such quantities that for one isocyanate group there is 0.8-1.0 moles of cyclic amidine.

14. A process according to claim 3 wherein after said reaction with polyvalent chain extension agents, the excess chain extension agent is either removed by itself or in combination with a used solvent.

15. The process of claim 1 wherein said polyisocyanate is selected from the group consisting of 3-isocyanatomethyl-3,5,5-trimethylcyclohexyl isocyanate, 2,4- and 2,6-toluylene-diisocyanate, and isomeric mixtures thereof.

16. A blocked polyisocyanate of the formula:

wherein R and R' are the same or different substituents selected from the group consisting of hydrogen, alkyl, cycloalkyl, benzyl and phenyl and
wherein either R' and R or 2 R' taken together form a cyclaliphatic ring, and R'' is the organic residue of a diol selected from the group consisting of ethylene glycol, 1,2-propanediol, 1,3-propanediol, 2,2-dimethyl-propanediol-1,3, butanediol-1,4, hexanediol-1,6,2,2,4-trimethylhexanediol-1,6, 2,4,4-trimethylhexanediol-1,6, heptanediol-1,7, octadecene-9,10-diol-1,12, thiodiglycol, octadecanediol-1,18, 2,4-dimethyl-2-propylheptanediol-1,3, butenediol-1,4, butynediol-1,4, diethylene glycol, triethylene glycol, tetraethylene glycol, trans-1,4-cyclohexanedimethanol, and 1,4-cyclohexanediol.

* * * * *